(12) United States Patent
Strobel

(10) Patent No.: US 6,810,280 B2
(45) Date of Patent: Oct. 26, 2004

(54) METHOD AND APPARATUS FOR DETECTING THE THREE-DIMENSIONAL POSITION OF AN EXAMINATION INSTRUMENT INSERTED INTO A BODY REGION

(75) Inventor: Norbert Strobel, Baiersdorf (DE)

(73) Assignee: SIEMENS Aktiengesellschaft, Munich (DE)

( * ) Notice: Subject to any disclaimer, the term of this patent is extended or adjusted under 35 U.S.C. 154(b) by 0 days.

(21) Appl. No.: 10/226,261

(22) Filed: Aug. 23, 2002

(65) Prior Publication Data
US 2003/0128800 A1 Jul. 10, 2003

(30) Foreign Application Priority Data

Aug. 23, 2001 (DE) .......................................... 101 41 406

(51) Int. Cl.⁷ ................................................ A61B 5/00
(52) U.S. Cl. ........................ 600/424; 600/426; 600/427
(58) Field of Search ................................ 600/407, 424, 600/425, 426, 427, 429; 378/20, 63, 68; 250/362, 370.08, 370.09, 370.1

(56) References Cited

U.S. PATENT DOCUMENTS 5,951,475 A * 9/1999 Gueziec et al. ............. 600/425
6,484,049 B1 * 11/2002 Seeley et al. ................ 600/426

FOREIGN PATENT DOCUMENTS

DE 694 19 134 1/2000
EP 0 680 277 11/1995

* cited by examiner

Primary Examiner—Ruth S. Smith
(74) Attorney, Agent, or Firm—Young & Thompson

(57) ABSTRACT

A method for detecting the three-dimensional position of an examination instrument inserted into a body region, on which instrument there are provided three markings whose mutual geometric arrangement is known, by using a device for recording radiation images with the aid of a radiation source and a radiation receiver, includes the steps of, recording two-dimensional projection image of the body region, determining the positions $(u_i, v_i)$ of the three markings in the projection image, and determining the spatial coordinates $(x_i, y_i, z_i)$ of the three markings in the coordinate system of the recording device with the aid of the positions $(u_i, v_i)$ and the projection matrix belonging to the projection image, taking into account the known mutual geometric arrangement of the markings.

10 Claims, 1 Drawing Sheet $F = (x_F, y_F, z_F)$ $X_a = (x_a, y_a, z_a)$ $X_b = (x_b, y_b, z_b)$ $X_c = (x_c, y_c, z_c)$

METHOD AND APPARATUS FOR DETECTING THE THREE-DIMENSIONAL POSITION OF AN EXAMINATION INSTRUMENT INSERTED INTO A BODY REGION

BACKGROUND OF THE INVENTION

The invention relates to a method for automatically detecting the three-dimensional position of a medical examination instrument inserted into a body region, by using a device for recording radiation images with the aid of a radiation source and a radiation receiver.

So that the physician, who is guiding an endoscope or similar rigid instrument, for example, can slide the latter into the desired target zone, it is necessary for him to receive information on the respective position and/or orientation of the instrument as it is being displaced. To date, the physician receives the relevant information with the aid of fluorograms, recorded with the aid of an X-ray system, of the examination or body region. Mostly, continuous fluorograms are recorded from two different directions and/or with the aid of two image planes at a mutual angle. These are displayed to the physician next to one another on a common monitor or two mutually adjacent monitors. These two images, whose image planes are mostly mutually perpendicular, can then be used by the physician to determine the position of the instrument and detect how the instrument is moving in the space. However, it is disadvantageous in this case that the physician must look simultaneously at two monitors and/or two images, in order to obtain the required information. A further disadvantage consists in that the two images are only projection images. That is to say, all the body parts are superimposed on one another in the direction of projection. As a result, it is therefore a complicated matter for the physician to detect the actually obtaining three-dimensional geometry with the aid of these two two-dimensional projection images, and to detect how the instrument is now actually positioned in the body region, and how and in which direction he must displace it further in order to reach the desired target zone.

As an alternative thereto, it is also known, particularly in the case of rigid examination instruments, which are those concerned in the present case, to make use of navigation systems. For this purpose, one or more navigation marks are fastened to stationary positions of the patient under examination, for example the skin, a bone or the like, and on the examination instrument whose position is to be detected. The known navigation systems use optical cameras and infrared light-emitting diodes in the markings. Other techniques use acoustic or magnetic sensors. Normally, all the positions are detected with reference to the coordinate system of the navigation system and subsequently converted into the coordinate system of the C-bow, in which the images are recorded. This method, too, is very complicated.

SUMMARY OF THE INVENTION

It is the object of the invention to specify a method which permits the three-dimensional position of an examination instrument to be determined in a simple way.

In order to solve this problem, a method of the type mentioned at the beginning is provided with the following steps:

recording at least one two-dimensional projection image of the body region, determining the positions $(u_i, v_i)$ of at least three radiatively opaque markings shown in a projection image, and determining the spatial coordinates $(x_i, y_i, z_i)$ of the markings in the coordinate system of the recording device with the aid of the positions $(u_i, v_i)$ and the projection matrix belonging to the projection image, taking account of the known mutual geometric arrangement of the markings.

The invention offers the possibility of being able to use only one projection image to detect the three-dimensional position of an examination instrument in the coordinate system of the C-bow. With the aid of a two-dimensional projection image in which the at least three radiatively opaque markings arranged on the examination instrument are to be seen, their two-dimensional positions $u_i$, $v_i$ in the projection image are firstly determined, and thus those in the plane of the radiation detector are determined. The mutual geometric arrangement of the markings is known in this case, that is to say it is known how the markings are mutually positioned in space and how they are arranged on the instrument. With the aid of the projection matrix, which must be known in relation to the projection image to be processed and contains all the relevant geometric data with regard to the tube and detector positions etc., relative to those in the respective projection image, it is now possible to use the determined marking positions in the projection image and the known geometric relationships with regard to the arrangement of the markings to determine where these are in space. The point is that the positions of the projections of the markings in the projection image are naturally a function of their position in space, while they are located in the beam path between the focus of the radiation source and the detector plane.

In this case, it is possible for the purpose of determining the spatial coordinates $(x_i, y_i, z_i)$ firstly to set up a set of linear equations for describing the direct connecting lines between the focus of the radiation source and the respective position $(u_i, v_i)$ in the projection image, after which the spatial coordinates are determined from the set of equations by taking account of the geometric arrangement.

The geometric or spatial arrangement of the markings on the examination instrument can be arbitrary, for example the markings can be positioned in a line with a defined line spacing. Other positionings are also conceivable. All that is important is that their mutual arrangement, that is to say the spacing and angle that they form relative to one another be known. Again, more than three markings can be used. All that need then be ensured is that it can be detected in the projection image which three markings—and at least three markings must be visible in the projection image in order to determine the spatial coordinates—are actually displayed so that the corresponding geometric data can be used in this context.

In order to be able to disseminate and display the detected information informatively, it is expedient, when a plurality of two-dimensional projections which were recorded before the insertion of the examination instrument are used firstly to create a three dimensional volumetric image of the body region in which the markings are displayed. That is to say, during the in situ detection of the marking coordinates, the latter can be displayed at once, after their determination, to the physician in the three dimensional volumetric image created, so that he knows precisely where the instrument is situated. The display of the markings is very sufficient, in particular, whenever these are arranged along a line on the instrument. Of course, it is also conceivable, in addition, to display the examination instrument itself in the volumetric image. Said instrument can be fitted into the volumetric image in the correct orientation without problems after the spatial coordinates of the markings, which are fastened permanently on the rigid examination instrument, are known.

In addition to the method according to the invention, the invention further relates to a device for recording radiation images, comprising a radiation source and a radiation receiver, and image recording and calculating means. The device according to the invention is designed for recording at least one two-dimensional projection image of a body region into which an examination instrument with at least three markings whose mutual geometric arrangement is known is inserted, for determining the positions ($u_i$, $v_i$) of the at least three radiatively opaque markings shown in a projection image, and for determining the spatial coordinates ($x_i$, $y_i$, $z_i$) of the at least three markings in the coordinate system of the recording device with the aid of the positions ($u_i$, $v_i$) and the projection matrix belonging to the projection image by taking account of the known mutual geometric arrangement of the markings.

In this case, the image recording and calculating means can be designed for determining the spatial coordinates ($x_i$, $y_i$, $z_i$) with the aid of a set of linear equations describing the direct connecting lines between the focus of the radiation source and the respective position ($u_i$, $v_i$) in the projection image by taking account of the geometric arrangement. Furthermore, it is possible to use the image recording and calculating means to insert either only the markings, or else the examination instrument itself into the volumetric image, which can be calculated with the aid of the two-dimensional projections. If the examination instrument is fitted in, it is expedient when there is stored in the image recording and calculating means a display of the examination instrument which is depicted in the volumetric image as a function of the determined spatial coordinates. Since, of course, the most varied examination instruments can be inserted into the body, it is expedient when images are stored which respectively correspond to the different types, can be selected or determined in advance on the part of the user and can then be depicted with accurate positioning.

BRIEF DESCRIPTION OF THE DRAWINGS

Further advantages, features and details of the invention emerge from the exemplary embodiment described below, as well as with the aid of the drawings, in which.

DESCRIPTION OF PREFERRED EMBODIMENTS

Figure 1:
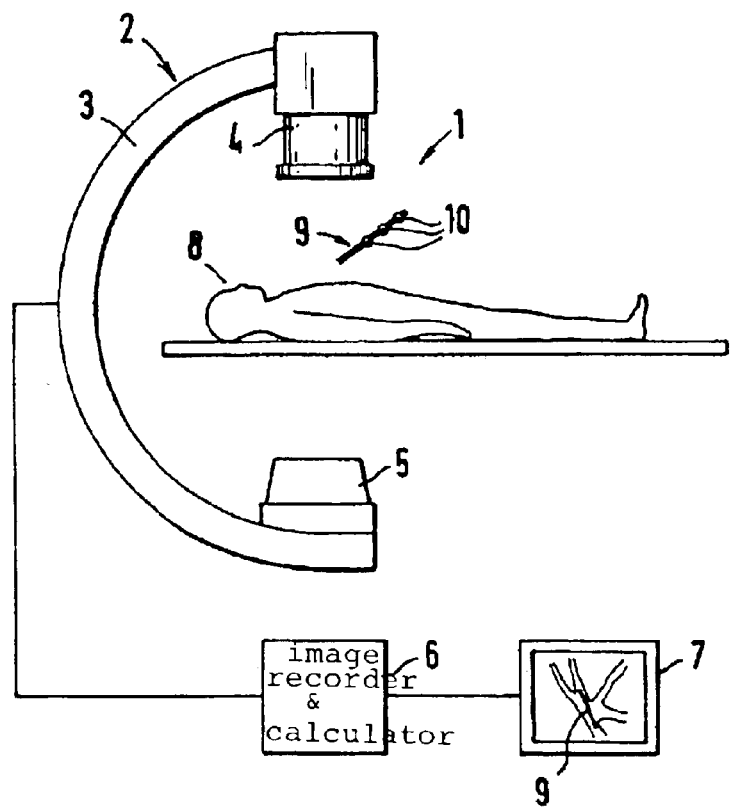
FIG. 1 shows a sketch of the principle of a device according to the invention.

In the form of a sketch of the principle, FIG. 1 shows a device according to the invention for carrying out the method according to the invention. This device 1 comprises a C-bow system 2 with a C-bow 3, on which a radiation source 4 and a radiation detector 5 are arranged. The radiation source 4 is designed as an x-ray machine, and the radiation detector 5 an x-ray image intensifier or as a flat panel image detector.

In order to control the image recording operation and to determine the images to be output, an image recording and calculating means 6 is provided which is used to control all relevant functions, be this the movement of the C-bow or the control of the radiation source and of the radiation detector, as well as the determination of coordinates and the actual determination and output of images. The output of images itself is performed on a monitor 7.

A rigid medical instrument 9, that is to say one having a rigid instrument body, is to be inserted into the patient 8 under continuous observation. Three radiatively opaque markings 10 are arranged in a stable position on the instrument 9 in the exemplary embodiment shown. The geometric arrangement of the markings 10 on the instrument body is known. In the example shown, the markings 10 are arranged in a line and spaced apart mutually in each case by a predetermined known length l. It may be assumed that the markings 10 are named "a, b, c" in series. The spacing from marking to marking is then defined as $l_{ab}$, $l_{ac}$ and $l_{bc}$.

For the purpose of continuous monitoring of the position of the examination instrument 9, the fixed C-bow system 2 is now used to record continuously the body region into which the examination instrument 9 is to be inserted. The C-bow system supplies a set of two-dimensional projection images in temporal sequence. In order to determine the actual position of the examination instrument 9, a projection image P is now taken from the series of the protection images and analyzed. This is illustrated in detail in FIG. 2.

Figure 2:
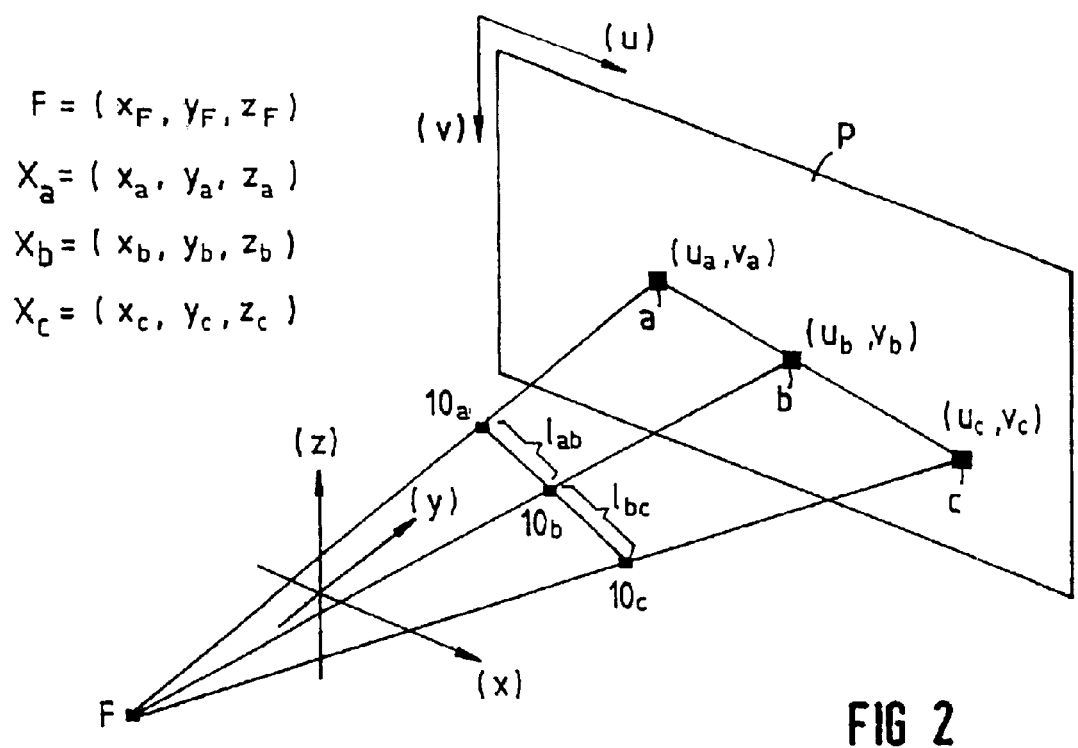
FIG. 2 shows a sketch of the principle for the purpose of explaining the determination of the spatial coordinates.

The projection image P that is to say the detector image, is shown as it was recorded from the body region in relation to a specific position of the radiation source 4 and the radiation detector 5. Visible in the projection image P are the three markings 10, which are denoted there by a, b, c. The position of the markings a, b, c in the projection image P can be described with the aid of the position data ($u_a$, $v_a$), ($u_b$, $v_b$) and ($u_c$, $v_c$) in the two-dimensional image plane, as shown in FIG. 2.

Also known in relation to the known projection image P is the projection matrix in which there are contained the more detailed information with regard to the position of the radiation source and of the radiation detector in the C-bow system coordinate system, and other relevant image recording information. The three markings as they are arranged on the examination instrument are denoted in FIG. 2 by 10a, 10b and 10c. So that they can be imaged in the projection image P, they must necessarily be situated in the beam path between the focus of the radiation source 4 and the detector plane. With the aid of the projection matrix, which contains, inter alia, the position of the focus of the radiation source 4 relative to the given projection P (the focus is denoted by F in FIG. 2), as well as with the aid of the known geometric boundary conditions on the basis of the relevant mutual position of the markings 10a, 10b and 10c, it is now possible to calculate the actual spatial coordinates $X_a=(x_a, y_a, z_a)$ for the marking 10a, $X_b=(x_b, y_b, z_b)$ for the marking 10b and $X_c=(x_c, y_c, z_c)$ for the marking 10c, the markings 10a, b, c being constrained to lie on a direct line from the focus F to the respective point a, b, c in the projection image P. The determination of the spatial coordinates $X_a$, $X_b$ and $X_c$ is performed in the coordinate system (x, y, z) of the C-bow system 2.

If, now the coordinates $X_a$, $X_b$ and $X_c$ are known, then, since the markings are arranged permanently on the examination instrument 9, it is necessarily possible therefrom for the exact position of the examination instrument 9 in the coordinate system (x, y, z) to be determined.

For the purpose of the display which can be evaluated by the physician, it is now possible to reconstruct a three-dimensional volume with the aid of two-D-projection images, recorded before the intervention, with the rotating C-bow, for which purpose known reconstruction methods are used. The display of the three-dimensional volumetric image is performed on the monitor 7. Furthermore, now, after the determination of the spatial coordinates of the examination instrument 9, said instrument is depicted in the correct position in the three-dimensional volume shown on the monitor 7. It is expedient for this purpose to store in the image recording and calculating means a set of different examination instruments such that the examination instrument that is correct because of its design and its dimensions can be fitted into the volumetric image directly in terms of position and dimensions.

What is claimed is:

1. A method for detecting the three-dimensional position of an examination instrument inserted into a body region, on which instrument there are provided at least three radiatively opaque markings whose mutual geometric arrangement is known, by using a recording device for recording radiation images with the aid of a radiation source and a radiation receiver, the method comprising the steps of:

recording one two-dimensional projection image of the body region, determining positions ($u_i$, $v_i$) of the at least three radiatively opaque markings shown in the one projection image, and determining spatial coordinates ($x_i$, $y_i$, $z_i$) of the at least three markings in a coordinate system of the recording device with the aid of the positions ($u_i$, $v_i$) and a projection matrix belonging to only the one projection image, taking into account the known mutual geometric arrangement of the markings.

2. The method as claimed in claim 1, wherein a set of linear equations for describing direct connecting lines between a focus of the radiation source and the respective position ($u_i$, $v_i$) in the projection image is set up in order to determine the spatial coordinates ($X_i$, $y_i$, $z_i$).

3. The method as claimed in claim 1, wherein the examination instrument has the at least three markings arranged in a line therein.

4. The method as claimed in claim 1, comprising the step of recording a plurality of two-dimensional projections to create a three-dimensional volumetric image of the body region in which the markings are displayed.

5. The method as claimed in claim 1, wherein the examination instrument is displayed in volumetric image.

6. A device for recording radiation images, comprising:

a radiation source (4) and a radiation receiver (5), and an image recording and calculating means (6) for recording one two-dimensional projection image (2) of a body region into which an examination instrument (9) with at least three markings (10a, 10b, 10c) whose mutual geometric arrangement is known is inserted, determining positions ($u_i$, $v_i$) of the at least three radiatively opaque markings shown in the one projection image (P), and determining spatial coordinates ($X_i$, $y_i$, $z_i$) of the at least three markings in a coordinate system of the recording device with the aid of the positions ($u_i$, $v_i$) and a projection matrix belonging to only the one projection image (P) by taking into account the known mutual geometric arrangement of the markings (10a, 10b, 10c).

7. The device as claimed in claim 6, wherein the image recording and calculating means (6) is for determining the spatial coordinates ($x_i$, $y_i$, $z_i$) with the aid of a set of linear equations describing direct connecting lines between a focus (F) of the radiation source (4) and the respective position ($u_i$, $v_i$) in the projection image (P).

8. The device as claimed in claim 6, wherein the image recording and calculating means (6) is for determining a three-dimensional volumetric image with the aid of two-dimensional projections (P), and for displaying the markings (10a, 10b, 10c) in the volumetric image.

9. The device as claimed in claim 6, wherein the image recording and calculating means (6) is for determining a three-dimensional volumetric image with the aid of two-dimensional projections, and for displaying the examination insttument (9) in the volumetric image.

10. The device as claimed in claim 9, wherein said image recording and calculating means (6) comprises a display of the examination instrument (9) which is depicted in the volumetric image as a function of the determined spatial coordinates.

* * * * *